United States Patent
Doebert et al.

(10) Patent No.: US 6,169,781 B1
(45) Date of Patent: Jan. 2, 2001

(54) SENSOR THAT CAN BE PLACED INTRAORALLY IN THE MOUTH OF A PATIENT FOR THE PRODUCTION OF TOOTH/JAW EXPOSURES OF A PATIENT

(75) Inventors: Michael Doebert; Tilman Phleps, both of Lorsch; Uwe Zeller, Neu Anspach, all of (DE)

(73) Assignee: Sirona Dental Systems GmbH & Co. KG, Bensheim (DE)

( * ) Notice: Under 35 U.S.C. 154(b), the term of this patent shall be extended for 0 days.

(21) Appl. No.: 09/163,615

(22) Filed: Sep. 30, 1998

(30) Foreign Application Priority Data

Sep. 30, 1997 (DE) .................................................. 29717432

(51) Int. Cl.⁷ ........................................................ A61B 6/14
(52) U.S. Cl. .......................................... 378/98.8; 378/189
(58) Field of Search ..................... 378/98.8, 189, 378/167, 191, 168, 169, 190; D24/158

(56) References Cited

U.S. PATENT DOCUMENTS

| | | | |
|---|---|---|---|
| D. 361,619 | 8/1995 | Phleps et al. . | |
| D. 409,307 | * 5/1999 | Phleps et al. | .......................... D24/158 |
| 1,748,490 | * 2/1930 | Martin | .................................. 378/169 |
| 2,104,715 | * 1/1938 | Saffir | ..................................... 378/169 |
| 3,851,178 | * 11/1974 | Borden | ................................. 378/169 |
| 5,510,623 | * 4/1996 | Sayag et al | .......................... 378/98.8 |

FOREIGN PATENT DOCUMENTS 93 19 391    7/1994  (DE) .

OTHER PUBLICATIONS

Brochure for VISUALIX Digital Video Radiographic System, Philips Medical Systems No date.
Brochure for SENS–A–Ray Dental X–ray Imaging System, Regam Medical Systems AB No date.

* cited by examiner

Primary Examiner—David P. Porta
(74) Attorney, Agent, or Firm—Schiff Hardin & Waite

(57) ABSTRACT

A sensor that can be placed intraorally in the mouth of a patient for the production of tooth/jaw exposures of a patient has a narrow housing, approximately rectangular in a top view, for an image detector and a control circuit board to which lines are connected, which can be connected, with a free end, with an image processing unit via a connecting cable exiting from the housing at the back wall of the housing. At least one narrow side of the housing has a rounded shape that is adapted to the anatomical characteristics of the upper jaw of an average patient.

4 Claims, 1 Drawing Sheet

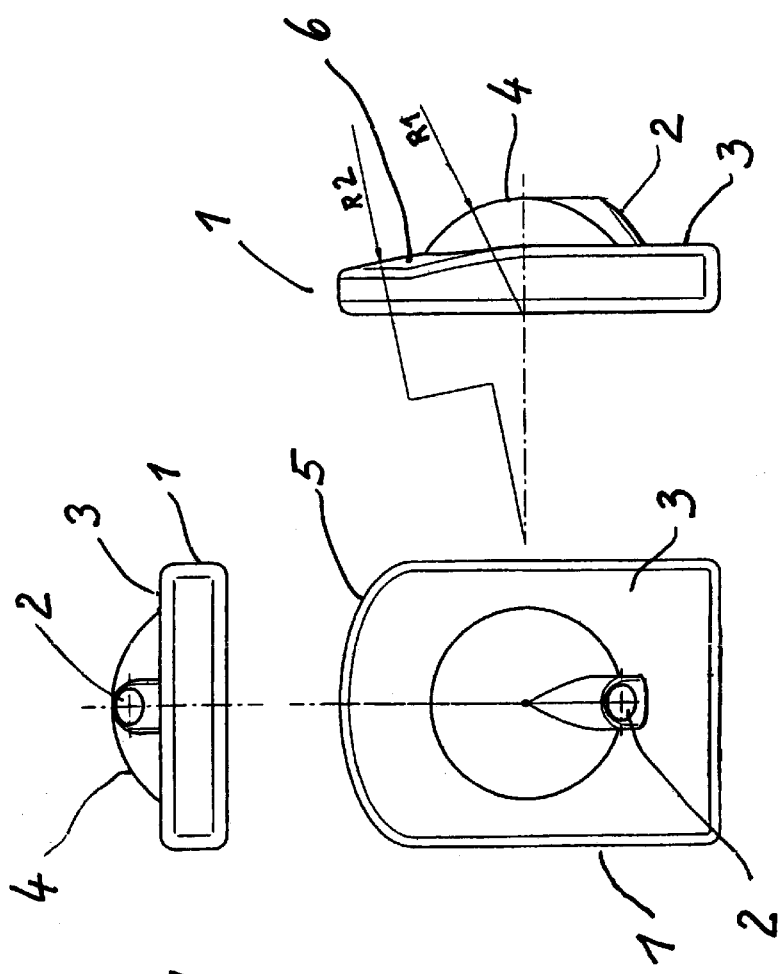
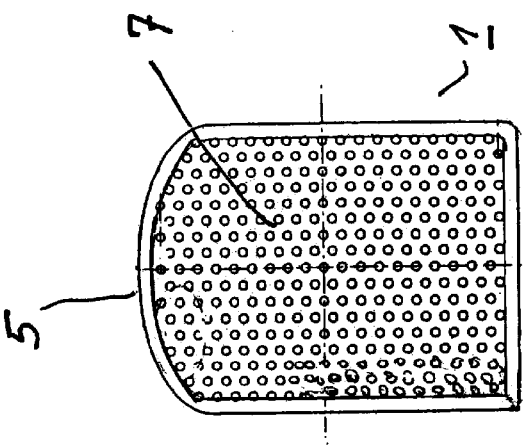
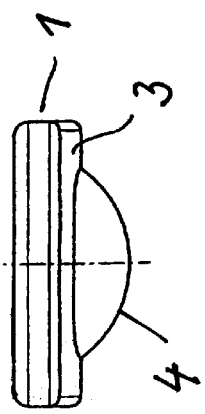

SENSOR THAT CAN BE PLACED INTRAORALLY IN THE MOUTH OF A PATIENT FOR THE PRODUCTION OF TOOTH/JAW EXPOSURES OF A PATIENT

BACKGROUND OF THE INVENTION

1. Field of the Invention

The present invention is directed to a sensor of the type that can be placed intraorally in the mouth of a patient for the production of tooth/jaw exposures of the patient, and in particular to a sensor of this type having a narrow, generally rectangular housing for an image detector, and a control circuit board to which various lines of a connection cable are connected, whose free end can be connected with an image processing unit.

2. Description of the Prior Art

Intraoral sensors of the above type are known for example from the publications entitled "VISUALIX the new way to take dental X-rays," of the company Philips Medical Systems, and "SENS-A-RAY a revolution in dental radiography," of the company Regam Medical Systems AB, as well as from DE-GM 93 19 391. In the known embodiments, the connection cable required for controlling the image detector exits either at the frontal side of the narrower side wall of the housing, or at a right angle; or at an acute angle thereto, at the rear wall of the housing.

Larger sensors, exceeding the currently standard size of approx. 22.3×27.3 mm, are, apart from the cable routing, particularly problematic with respect to the positioning of the sensor in the oral cavity of the patient, especially if the production of exposures in the front tooth region or in the rear molar region is desired.

SUMMARY OF THE INVENTION

An object of the present invention is to provide an improved sensor of this type by providing a sensor that permits better placement of the sensor in the mouth of the patient, in particular for the exposures mentioned above.

According to the invention, at least one side of the sensor has a shape adapted to the curve of the palate, and thus has no disturbing edges, even with beveling of the sensor edges, which may be perceived as unpleasant by the patient. The shape can be circular, elliptical, or paraboloid. The cable exit of the connecting cable runs, in a known manner, obliquely to the longitudinal plane of the housing, or to the sensor plane, so that an optimal positioning of the sensor is achieved for almost all dental exposures. The sensor can be provided at least on one narrow side, such as the back side of the housing, with a smoothing that permits better adaptation of the sensor in molar exposures. The smoothing can be fashioned as a circular arc with a relatively large radius. The front side of the sensor can advantageously be constructed so that the active surface of the image detector is made outwardly visible and/or able to be felt by means of design elements.

DESCRIPTION OF THE DRAWINGS

FIG. 1 is a bottom view of an intraoral sensor in accordance with the invention.

FIG. 2 is a rear view of the intraoral sensor of FIG. 1.

FIG. 3 is a top view of the intraoral sensor of FIGS. 1 and 2.

FIG. 4 is a side view of the intraoral sensor of FIGS. 1, 2 and 3.

FIG. 5 is a front view of the intraoral sensor of FIGS. 1, 2, 3 and 4.

DESCRIPTION OF THE PREFERRED EMBODIMENTS

FIGS. 1 to 5 show various views of an embodiment of the inventive intraoral sensor. In a housing 1, which is approximately rectangular in the top view (FIG. 3), an image detector such as a CCD sensor (not shown) is housed, which is connected in a suitable manner with a control circuit board. Lines that are conducted out from the housing 1 at a terminal part 2, via a cable (not shown), and can be connected with an image processing unit (not shown). The control circuit board, which contains various electronic components, is well-known and thus need not be described in more detail.

The cable exit of the connecting cable takes place in a known manner at the rear wall 3 of the housing 1 at an angle between 20° and 60° to the longitudinal axis of the housing 1. As can be seen from the figures, in the region of the cable exit the housing 1 has a convex curvature with a radius R1, in the shape of a cap 4 integrally formed on the housing 1.

The housing 1, approximately rectangular in the top view of FIG. 3, is rounded at least at the narrow side opposite the cable exit. The rounding is adapted to the anatomical characteristics of the upper jaw, i.e. to the curvature of the palate or roof of the mouth of an average patient. This shaping enables an optimal positioning of the sensor, in particular for exposures of dental root apexes (as well as crowns) without its presence being perceived as unpleasant by the patient. The rounding can have the shape of a circle, an ellipse, or a parabola. Likewise, in the region of this narrow side the housing 1 has a smoothing or indentation 6 formed by a relatively large radius R2. This smoothing makes possible a better placement of the sensor between the tongue and the tooth in molar exposures. The front side of the sensor is in addition also provided with a surface 7 that can be seen and/or felt by means of design elements, e.g. circles, points, or the like. This surface is substantially congruent with the contour of the image detector, which is located in the interior of the housing 1 and is thus not visible. The surface 7 thus provides an exterior visual and/or tactile identification of the location of the hidden image detector.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a sensor adapted for intraoral placement in a mouth of a patient for production of tooth/jaw exposures, said sensor having a housing containing an image detector and a control circuit board connected to said image detector and connected to a cable terminal disposed at a back wall of said housing for connection to an image processing unit located remote from said sensor, said housing having at least one narrow side, the improvement comprising:

said at least one narrow side forming a rounded region with an elliptical shaped and being adapted to anatomical characteristics of an upper jaw of an average patient;

said back wall of said housing having an indented region merging with said rounded region of said at least one narrow side.

2. In a sensor adapted for intraoral placement in a mouth of a patient for production of tooth/jaw exposures, said sensor having a housing containing an image detector and a control circuit board connected to said image detector and connected to a cable terminal disposed at a back wall of said housing for connection to an image processing unit located remote from said sensor, said housing having at least one narrow side, the improvement comprising:

said housing having a front side containing a plurality of visually perceptible elements substantially co-extensive with a contour of said image detector contained in said housing.

3. In a sensor adapted for intraoral placement in a mouth of a patient for production of tooth/jaw exposures, said sensor having a housing containing an image detector and a control circuit board connected to said image detector and connected to a cable terminal disposed at a back wall of said housing for connection to an image processing unit located remote from said sensor, said housing having at least one narrow side, the improvement comprising:

said housing having a front side containing a plurality of tactilely perceptible elements substantially co-extensive with a contour of said image detector contained in said housing.

4. The improvement of claim 1 wherein said housing has an integrally formed convex curvature at which said cable terminal is disposed, said integrally formed convex curvature covering at least said cable terminal.

* * * * *